US012453542B2

(12) United States Patent
Chen et al.

(10) Patent No.: US 12,453,542 B2
(45) Date of Patent: Oct. 28, 2025

(54) SHEATH ADAPTER AND SURGICAL ASSISTANCE SYSTEM

(71) Applicant: ROBGENIX MEDICAL PTE. LTD., Singapore (SG)

(72) Inventors: Hao Chen, Shanghai (CN); Cunwang Ge, Shanghai (CN); Gang Wu, Shanghai (CN); Xueting Wei, Shanghai (CN)

(73) Assignee: ROBGENIX MEDICAL PTE. LTD., Singapore (SG)

( * ) Notice: Subject to any disclaimer, the term of this patent is extended or adjusted under 35 U.S.C. 154(b) by 0 days.

(21) Appl. No.: 19/035,147

(22) Filed: Jan. 23, 2025

(65) Prior Publication Data

US 2025/0228536 A1 Jul. 17, 2025

Related U.S. Application Data

(63) Continuation of application No. PCT/CN2024/138219, filed on Dec. 10, 2024.

(30) Foreign Application Priority Data

Dec. 11, 2023 (CN) ........................ 202311696447.2

(51) Int. Cl.
*A61B 17/00* (2006.01)

(52) U.S. Cl.
CPC .................. *A61B 17/00234* (2013.01); *A61B 2017/00323* (2013.01); *A61B 2017/00336* (2013.01)

(58) Field of Classification Search
CPC .... A61B 17/00234; A61B 2017/00323; A61B 2017/00336; A61B 17/00; A61B 1/00; A61B 34/35
See application file for complete search history.

(56) References Cited

U.S. PATENT DOCUMENTS 5,738,666 A * 4/1998 Watson ............ A61M 25/0074 604/247

FOREIGN PATENT DOCUMENTS

| | | |
|---|---|---|
| CN | 113520611 A | 10/2021 |
| CN | 115363766 A | 11/2022 |

(Continued)

OTHER PUBLICATIONS

Written Opinion of the International Searching Authorization and International Search Report mailed Mar. 15, 2025 in International Application No. PCT/CN2024/138219, with English translation, 17 pages.

*Primary Examiner* — Niketa Patel
*Assistant Examiner* — Sebastian X Lukjan
(74) *Attorney, Agent, or Firm* — Nixon & Vanderhye P.C.

(57) ABSTRACT

A sheath adapter for a surgical assistance system includes a support frame, a telescopic rod assembly and a cap. The rod assembly includes a movable shaft and a rotating shaft which has a first end rotatably connected to the support frame and a second end slidably connected to a first end of the movable shaft. The cap includes a groove for receiving a knob and is connected to a second end of the movable shaft. The rotating shaft is rotatable to cause the rotation of the cap via the movable shaft. The movable shaft is slidable in an axial direction to adjust the position of the cap relative to the support frame. The sheath adapter and the rod assembly are configured to form clearance to allow placement of a surgical instrument on the support frame and attachment of the knob of the surgical instrument via the cap to allow assembly.

10 Claims, 5 Drawing Sheets

(56) References Cited

FOREIGN PATENT DOCUMENTS

| | | | |
|---|---|---|---|
| CN | 115644771 | A | 1/2023 |
| CN | 219109850 | U | 6/2023 |
| CN | 219109851 | U | 6/2023 |
| CN | 117379233 | A | 1/2024 |
| CN | 117530766 | A | 2/2024 |
| CN | 221555881 | U | 8/2024 |
| KR | 20170115822 | A | 10/2017 |
| KR | 20180044627 | A | 5/2018 |

* cited by examiner

SHEATH ADAPTER AND SURGICAL ASSISTANCE SYSTEM

CROSS-REFERENCE TO RELATED APPLICATIONS

The present application is a continuation of International Application No. PCT/CN2024/138219 filed Dec. 10, 2024, which designated the U.S. and claims priority to CN application number 202311696447.2, filed on Dec. 11, 2023, and entitled "Sheath Adapter and Surgical Assistance System". The entire contents of each of which are hereby incorporated by reference.

TECHNICAL FIELD

The present disclosure relates to the technical field of medical devices, and more particularly to a sheath adapter and surgical assistance system.

BACKGROUND

Minimally invasive surgery refers to surgery performed using modern medical devices and related equipment such as laparoscope and thoracoscope. Minimal trauma, light pain, and quick recovery desired for every patient requiring surgery, and minimally invasive surgery has made this dream a reality. During minimally invasive surgery, the intervention of passive minimally invasive surgical instruments is generally required. Passive minimally invasive surgical instruments can be understood as medical devices which do not rely on any electric energy or other energy source, but are directly produced by human body or gravity to perform their functions, but instead function by energy generated directly by the human body or gravity, that is, they require manual operation by the doctor. When it is necessary to complete some complicated surgical procedures or operate complicated minimally invasive surgical instruments, it is necessary for the doctor to have high level of technical skill and clinical experience, and it is difficult in operation and long in surgery time. In order to ensure that the smooth progress of the surgery, a dedicated power unit is used to control the minimally invasive surgical instruments to do the surgery.

At present, minimally invasive surgical instruments are typically operated by a knob that is rotated to control the motion of the distal end of the surgical instrument to complete the surgery. In the prior art, minimally invasive surgical instruments typically achieve transmission connection with the power unit via one sheath adapter. In order to ensure the transmission accuracy, the existing sheath adapter is usually connected with the minimally invasive surgical instrument through the meshing of worm gears and worms, that is, the shape of the knob is designed as the worm gear. However, even if the knob angles of the minimally invasive surgical instruments of the same type and specification are different, it is necessary to repeatedly adjust the angular orientation of the worm of the sheath adapter for each assembly to ensure that the worm gear teeth on the knob mesh with the worm of the sheath adapter accurately, thus ensuring the transmission accuracy. Specifically, every time the angle of the worm is adjusted, it is necessary to try to assemble the knob and the worm, and to observe whether they mesh accurately. If they do not meet the meshing requirements, it is necessary to readjust the angle of the worm until they meet the meshing requirements, which results in poor assembly convenience.

SUMMARY

It is an object of the present invention to provide a sheath adapter that facilitates assembly with a surgical instrument.

In order to achieve this object, the present invention adopts the following technical solutions:

A sheath adapter is provided, which includes:

a support frame;

a telescopic rod assembly including a rotating shaft and a movable shaft, where a first end of the rotating shaft is rotatably connected to the support frame, and a second end of the rotating shaft is slidably connected to a first end of the movable shaft; and a cap including a receiving groove, where the cap is connected to a second end of the movable shaft, the rotating shaft is rotatable to cause the rotation of the cap via the movable shaft, and the movable shaft is slidable in an axial direction to adjust the position of the cap with respect to the support frame.

Alternatively, one of the rotating shaft and the movable shaft is provided with a sliding channel, and the other is slidably inserted in the sliding channel.

Alternatively, a limiting slot is provided in a groove wall of the receiving groove.

Alternatively, the sheath adapter further includes a deceleration assembly having a first end connected to the movable shaft and a second end connected to the cap, where the rotating shaft is rotatable to cause the rotation of the cap via the movable shaft and the deceleration assembly.

Alternatively, the sheath adapter further includes:

a telescopic sleeve assembly in which the telescopic rod assembly is provided, where the telescopic sleeve assembly includes a fixed sleeve fixedly connected to the support frame and a movable sleeve connected to the fixed sleeve, the movable sleeve is rotatable and slidable with respect to the fixed sleeve, and the movable sleeve is rotatably connected to the movable shaft; and a cantilever having a first end fixedly connected to the movable sleeve and a second end on which the cap is provided, where the deceleration assembly is provided in the cantilever.

Alternatively, the sheath adapter further includes a fastener extending through the fixed sleeve and abutting against the movable sleeve, the fastener being threadedly connected to the fixed sleeve.

Alternatively, at least one sliding groove extending in an axial direction of the fixed sleeve is provided in the fixed sleeve, a circumferential slot communicating with the sliding groove is provided in an end of the fixed sleeve which faces the movable sleeve, and a slider portion corresponding to the sliding groove one-to-one is provided in an end of the movable sleeve which faces the fixed sleeve, and the slider portion is slidably provided in the sliding groove or the circumferential slot.

Alternatively, the sheath adapter further includes a sterile barrier detachably provided on the support frame, where the sterile barrier is provided in contact with the support frame.

Alternatively, a transmission shaft is rotatably provided on the sterile barrier and has a first end detachably connected to the rotating shaft, and the transmission shaft is rotatable to cause the rotation of the rotating shaft.

Another object of the present invention is also to provide a surgical assistance system including: the sheath adapter of any of the above; and a power unit, where the sheath adapter is detachably provided on the power unit, and the power unit comprises an output shaft, where the output shaft is rotatable to cause the rotation of the rotating shaft.

Technical Effects

The present disclosure provides a sheath adapter, during assembly of the sheath adapter with a surgical instrument, the surgical instrument is placed on the support frame, the movable shaft is slid, and the cap is moved toward the knob of the surgical instrument until the knob of the surgical instrument is placed within the receiving groove or against the cap. If the knob abuts against the cap, the rotating shaft is rotatable to cause the rotation of the cap via the movable shaft until the angle of the cap is adapted to receive the knob, and the movable shaft is slid again so that the knob is placed in the receiving groove to facilitate assembly. In addition, the arrangement of the telescopic rod assembly (that is, the sliding connection between the rotating shaft and the movable shaft) can form clearance, facilitating the placement of a surgical instrument on the support frame to prevent positional interference between the surgical instrument and the sheath adapter from affecting assembly.

The present disclosure provides a surgical assistance system that effectively ensures convenience of assembly between the sheath adapter and the surgical instrument.

Figure 1:
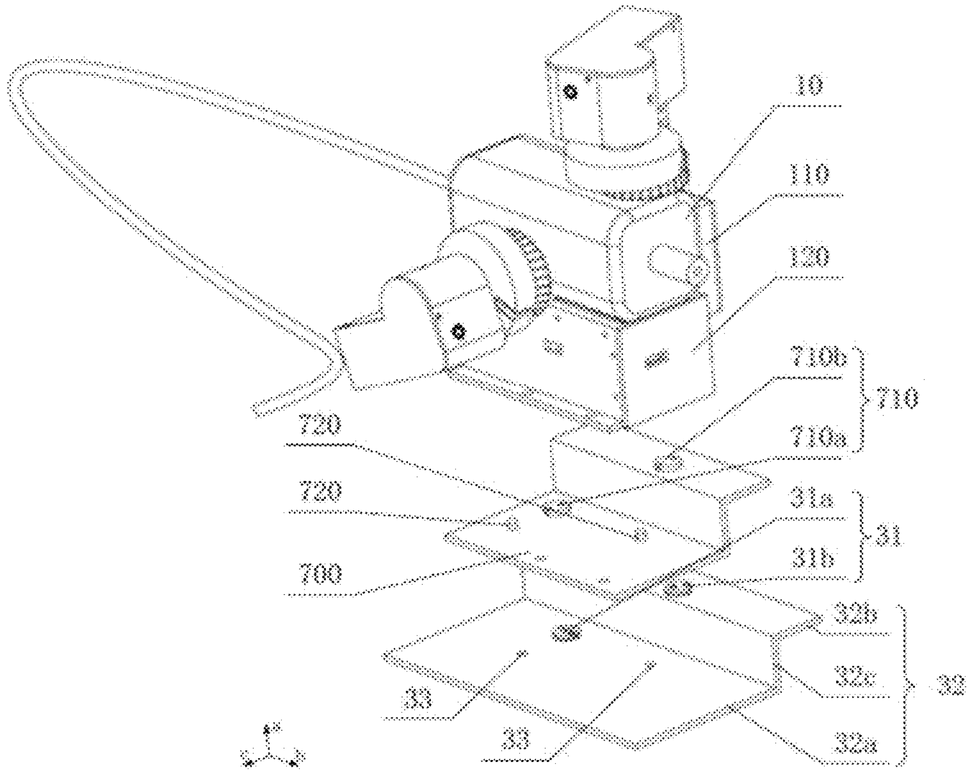
FIG. 1 is an exploded view of a surgical assistance system according to the present disclosure.

10. surgical instrument; 11. handle; 12. knob; 12*a*. first knob; 12*b*. second knob;

20. sheath adapter;

31. output shaft; 31*a*. first output shaft; 31*b*. second output shaft; 32. installation platform; 32*a*. first platform; 32*b*. second platform; 32*c*. side plate; 33. pin hole;

100. support frame; 101. input end; 101*a*. first input end; 101*b*. second input end; 1011. first protrusion; 102. fixing portion; 1021. fixing hole; 110. first frame body; 120. second frame body;

200. telescopic rod assembly; 210. rotating shaft; 211. sliding channel; 220. movable shaft;

300. cap; 310. receiving groove; 311. fixed slot; 320. limiting slot; 321. limiting surface;

400. deceleration assembly; 410. first bevel gear; 420. second bevel gear; 430. worm; 440. worm gear;

500. telescopic sleeve assembly; 510. fixed sleeve; 511. sliding groove; 512. circumferential slot; 520. movable sleeve;

521. slider portion;

600. cantilever;

700. sterile barrier; 710. transmission shaft; 710*a*. a first transmission shaft; 710*b*. secondary transmission shaft;

720. positioning pin;

810. third bevel gear; 820. fourth bevel gear.

DETAILED DESCRIPTION

The following is a detailed description of the present disclosure in conjunction with the accompanying drawings and embodiments. It should be understood that, the specific embodiments described herein are merely for the purpose of explaining the present disclosure and are not intended to limit the present invention. In addition, it should be noted that, the drawings only illustrate parts related to the present invention and not the entire structure for clarity.

In the description of the present disclosure, unless otherwise explicitly specified or limited, the terms “connected to”, “connected”, and “fixed” should be broadly understood, for example, they can be understood as fixedly connected, detachably connected, or integrally formed, can be understood as mechanically or electrically connected, can be directly connected or indirectly connected through intervening media, or can be understood as connected through the use of two elements or the interaction of two elements. The specific meaning of the above terms in the present disclosure can be understood in detail by those skilled in the art.

In the present disclosure, unless otherwise expressly stated or limited, a first feature being “above” or “below” a second feature may include the first and second features being in direct contact, or that the first and second features being not in direct contact but being in contact through additional features between them. Further, a first feature being “on”, “above” and “over” a second feature may include the first feature being directly above and diagonally above the second feature, or simply indicate that the first feature is has a higher level than the second feature. The first feature being “under”, “below” and “beneath” a second feature includes the first feature being directly below and diagonally below the second feature, or simply indicate that the first feature has a lower level than the second feature.

In the description of the present embodiment, the terms such as “upper”, “lower”, “right”, which indicate orientations or positional relationships, are based on the orientations or positional relationships shown in the accompanying drawings, these terms are used merely for the convenience of description and to simplify the operation, and do not indicate or imply that the device or element must have a specific orientation, be constructed and operated in a specific orientation, and therefore should not be construed as limiting the present invention. Furthermore, the terms such as “first” and “second” are used merely for the purpose of distinction in description and do not have any special meaning.

Referring to FIGS. 1 to 4, the present embodiment provides a surgical assistance system for driving a surgical instrument 10 to perform surgical operations, the surgical assistance system including a sheath adapter 20 and a power unit on which the sheath adapter 20 is detachably provided. The power unit is in transmission connection to the sheath adapter 20, and the surgical instrument 10 can be in transmission connection to the power unit via the sheath adapter 20.

Specifically, the surgical instrument 10 includes a handle 11 and a knob 12 provided on the handle 11.

Specifically, the sheath adapter 20 includes a support frame 100, a telescopic rod assembly 200 and a cap 300, where the telescopic rod assembly 200 includes a rotating shaft 210 and a movable shaft 220, a first end of the rotating shaft 210 is rotatably connected to the support frame 100, and a second end of the rotating shaft 210 is slidably connected to a first end of the movable shaft 220; the cap 300 includes a receiving groove 310 for receiving a knob 12, and the cap 300 is connected to the second end of the movable shaft 220, the rotating shaft 210 is rotatable to cause the rotation of the cap 300 via the movable shaft 220, and the movable shaft 220 is slidable in an axial direction to adjust the position of the cap 300 with respect to the support frame 100.

Specifically, the power unit includes an output shaft 31, and the output shaft 31 is rotatable to cause the rotation of the rotating shaft 210.

In the present embodiment, convenience of assembly between the sheath adapter 20 and the surgical instrument 10 can be effectively ensured by providing the sheath adapter 20. Specifically, during assembly of the sheath adapter 20 with the surgical instrument 10, the surgical instrument 10 is placed on the support frame 100, the movable shaft 220 is slid, and the cap 300 is moved toward the knob 12 of the surgical instrument 10 until the knob 12 of the surgical instrument 10 is placed within the receiving groove 310 or against the cap 300. If the knob 12 abuts against the cap 300, the rotating shaft 210 is rotatable to cause the rotation of the cap via the movable shaft 220 until the angle of the cap is adapted to receive the knob 12, and the movable shaft 220 is slid again so that the knob 12 can be placed within the receiving groove 310 to facilitate assembly. In addition, the knob 12 is driven by the cap 300 to rotate, which is stable, reliable and with high precision, and the arrangement of the telescopic rod assembly 200 (that is, the rotating shaft 210 and the movable shaft 220 are slidably connected) can form clearance to facilitate placement of a surgical instrument 10 on the support frame 100 to prevent positional interference between the surgical instrument 10 and the sheath adapter 20 from affecting assembly.

Figure 4:
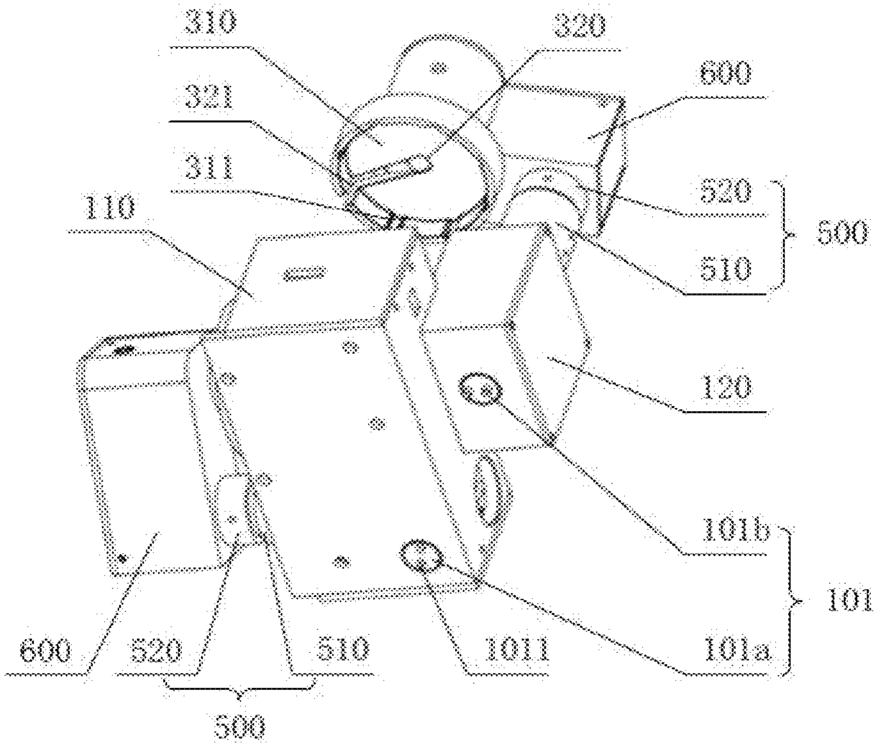
FIG. 4 is a schematic structural diagram illustrating a sheath adapter from another perspective according to the present disclosure.

In a possible embodiment, as shown in FIG. 4, one of the periphery of the knob 12 and the groove wall of the receiving groove 310 of the cap 300 is provided with a fixing slot 311 (not shown) at intervals, and the other is provided with a fixing protrusion (not shown) at intervals, and the fixing protrusion is provided in the fixing slot 311 to achieve a transmission adaptability of the knob 12 and the cap 300. For example, the fixing slot 311 and the fixing protrusion are respectively provided with at least one, and the fixing protrusions may be provided in the fixing slot 311 in one-to-one correspondence. The number of fixing slots 311 is greater than or equal to the number of fixing protrusions to facilitate assembly. It is obvious that, the shape of the periphery of the knob 12 and the groove wall of the receiving groove 310 may be other shapes, such as a wave shape, a polygon shape, a tooth shape, etc.

In a possible embodiment, as shown in FIG. 4, a limiting rod (not shown) is provided on the knob 12, a limiting slot 320 is provided in the groove wall of the receiving groove 310, and the limiting slot 320 is used for receiving the limiting rod. For example, the limiting slot 320 includes two limiting surfaces 321 parallel to each other and perpendicular to the center line of the cap 300, both of which are in abutment with the periphery of the limiting rod, effectively ensuring the transmission accuracy between the cap 300 and the knob 12. For example, the limiting rod and the limiting slot 320 are respectively provided with at least one, and the limiting slot 320 can receive the limiting rod in one-to-one correspondence.

For example, a limiting rod may be located at the periphery of the knob 12, a first end of the limiting rod is threadedly connected to the knob 12, and a second end of the limiting rod is provided with a head for pressing the cap 300 to form a fixed connection between the cap 300 and the knob 12, effectively ensuring transmission accuracy between the cap 300 and the knob 12. For example, the limiting rod may be a screw.

Figure 5:
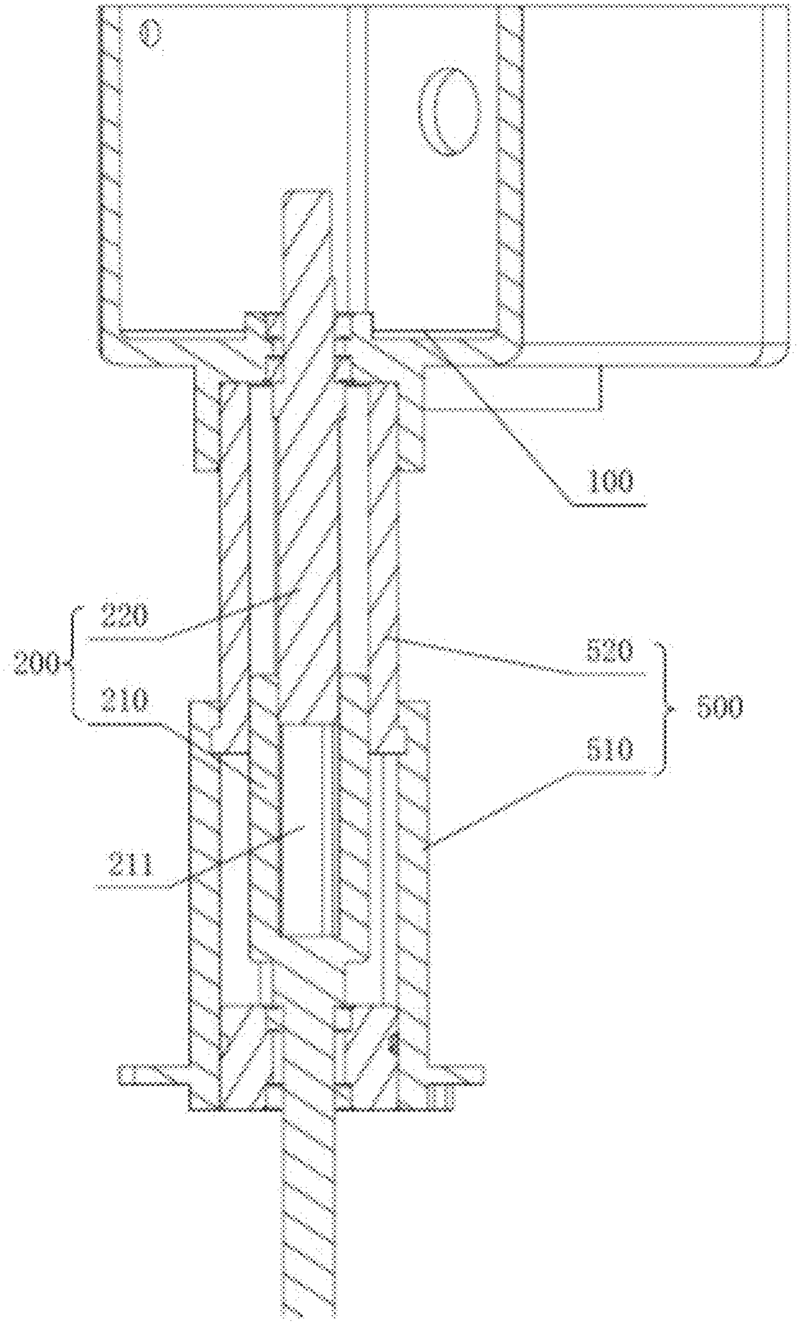
FIG. 5 is a partial structural cross-sectional view of a sheath adapter according to the present disclosure.

In a possible embodiment, as shown in FIG. 5, one of the rotating shaft 210 and the movable shaft 220 is provided with a sliding channel 211, and the other is slidably inserted into the sliding channel 211. Specifically, taking the example of the rotating shaft 210 provided with the sliding channel 211, an inner surface of the sliding channel 211 is provided in contact with the periphery of the movable shaft 220, effectively ensuring the coaxiality between the rotating shaft 210 and the movable shaft 220, and ensuring the sliding stability of the movable shaft 220 with respect to the rotating shaft 210. For example, an elongated slot (not shown) extending in the axial direction of the rotating shaft 210 is provided in the sliding channel 211, and an elongated protrusion (not shown) extending in the axial direction of the movable shaft 220 is provided in the periphery thereof, and the elongated protrusion is placed in the elongated slot for limiting, so that the movable shaft 220 can rotate together with the rotating shaft 210. It is obvious that, the shape of the sliding channel 211 may be spline-shaped, square-shaped, oval-shaped or other shapes, and the present application is not limited thereto.

Figure 6:
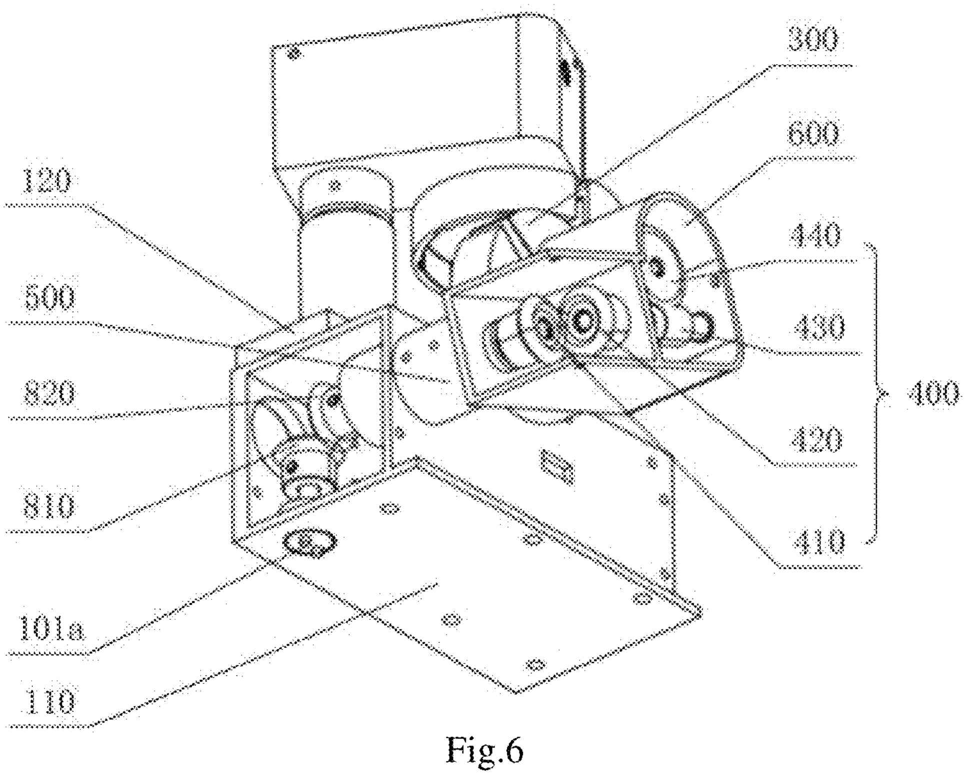
FIG. 6 is an inner schematic structural diagram illustrating a sheath adapter from a perspective according to the present disclosure.

In the present embodiment, as shown in FIG. 6, the sheath adapter 20 further includes a deceleration assembly 400 having a first end connected to the movable shaft 220 and a second end connected to the cap 300, and the rotating shaft 210 is rotatable to cause the rotation of the cap 300 via the movable shaft 220 and the deceleration assembly 400. In the present embodiment, the transmission ratio can be increased by providing the deceleration assembly 400 to ensure the accuracy of the transmission between the telescopic rod assembly 200 and the knob 12, and a smaller driving motor can be selected for the power unit. For example, first, the movable shaft 220 is pulled outward in a direction away from the support frame 100 to move the ratio wheel set and the cap 300 away from the support frame 100 to form clearance; then, the rotating shaft 210 is rotated so that the cap 300 corresponds to the knob 12; finally, the cap 300 is rotated so that the limiting rod corresponds to the limiting slot 320, and the movable shaft 220 is pushed back, so that the cap 300 is sleeved over the knob 12 to complete the assembly of the sheath adapter 20 and the knob 12, which is simple and convenient.

Specifically, the deceleration assembly 400 includes a first bevel gear 410, a second bevel gear 420, a worm 430, and a worm gear 440, where the first bevel gear 410 is provided on the second end of the movable shaft 220 and meshed with the second bevel gear 420, and the second bevel gear 420 is provided on the first end of the worm 430 meshed with the worm gear 440, and the worm gear 440 is connected to the first cap 300. For example, the rotation of the movable shaft 220 may drive the worm 430 to rotate through meshing between the first bevel gear 410 and the second bevel gear 420, and the worm 430 may drive the cap 300 to rotate through meshing transmission with the worm gear 440. In the present embodiment, the cap 300 is adapted to be assembled with the knob 12 through the meshing transmission of the first and second bevel gears 410 and 420 and the meshing transmission of the worm 430 and the worm gear 440 to change the orientation of the cap 300. In addition, the worm 430 and the worm gear 440 have a self-locking function, effectively ensuring stable and reliable transmission between the sheath adapter 20 and the knob 12.

Figure 7:
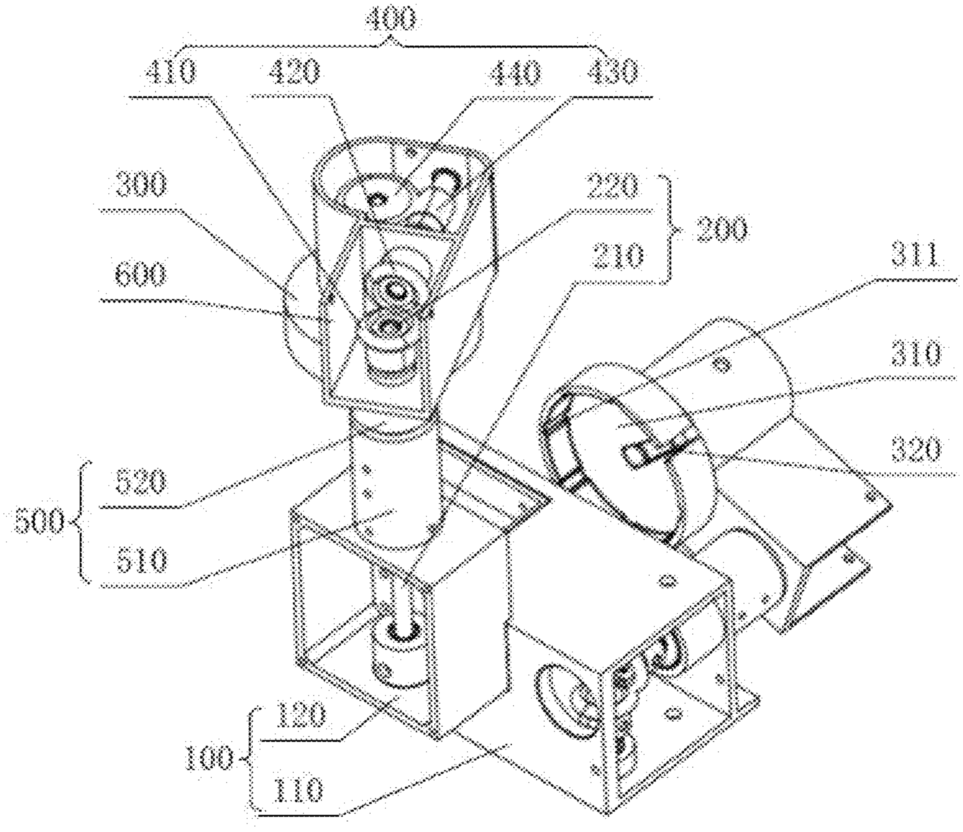
FIG. 7 is an inner schematic structural diagram illustrating a sheath adapter from another perspective according to the present disclosure.

In the present embodiment, referring to FIG. 7, the sheath adapter 20 further includes a telescopic sleeve assembly 500 and a cantilever 600, where a telescopic rod assembly 200 is provided in the telescopic sleeve assembly 500 and the telescopic sleeve assembly 500 includes a fixed sleeve 510 fixedly connected to a support frame 100 and a movable sleeve 520 connected to the fixed sleeve 510, the movable sleeve 520 is rotatable and slidable with respect to the fixed sleeve 510, and the movable sleeve 520 is rotatably connected to the movable shaft 220; the cantilever 600 has a first end fixedly connected to the movable sleeve 520 and a second end on which a cap 300 is provided, and the deceleration assembly 400 is provided in the cantilever 600. The movable sleeve 520 is slid with respect to the fixed sleeve 510, which can drive the movable shaft 220 to slide, thereby realizing the extension and retraction of the movable shaft 220 with respect to the rotating shaft 210; the movable sleeve 520 is rotatable to cause the rotation of the cantilever 600, allowing the cantilever 600 to move out of the way, and it is convenient to place the handle 11 on the support frame 100; by providing the telescopic sleeve assembly 500 and the cantilever 600, the cap 300 can be rotated directly, so that an angle of the cap is adapted to receive the knob 12, thereby facilitating assembly of the sheath adapter 20 with the knob 12.

In the present embodiment, the cantilever 600 provides support for the deceleration assembly 400 so that the transmission of the deceleration assembly 400 is stable and reliable. Specifically, the worm 430 and the worm gear 440 are both rotatably connected to the cantilever 600.

Figure 8:
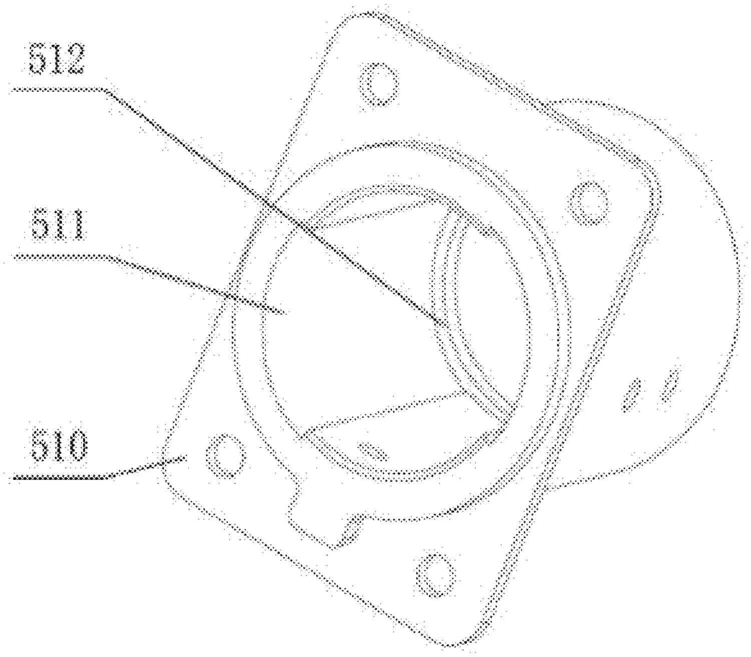
FIG. 8 is a schematic structural diagram illustrating a first fixed sleeve according to the present disclosure.
Figure 9:
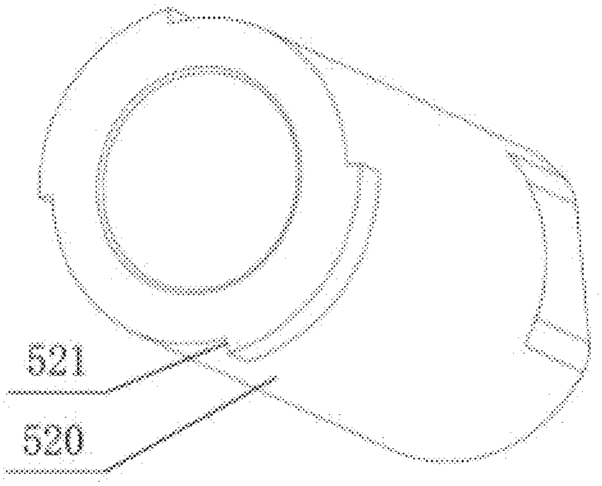
FIG. 9 is a schematic structural diagram illustrating a first movable sleeve according to the present disclosure.

In the present embodiment, as shown in FIGS. 5, 8 and 9, at least one sliding groove 511 extending in an axial direction of the fixed sleeve 510, for example, two sliding grooves 511 are provided in the fixed sleeve 510, a circumferential slot 512 communicating with the sliding groove 511 is provided in one end of the fixed sleeve 510 which faces the movable sleeve 520, and a slider portion 521 corresponding to the sliding groove 511 is provided in one end of the movable sleeve 520 which faces the fixed sleeve 510, and the slider portion 521 is slidably provided in the sliding groove 511 or the circumferential slot 512. For example, first, the movable sleeve 520 is pulled outward in a direction away from the support frame 100 so that the slider portion 521 slides from the sliding groove 511 into the circumferential slot 512, the movable sleeve 520 is rotated to move out of the way, and the handle 11 is placed on the support frame 100; then, the movable sleeve 520 is reversed, the slider portion 521 is aligned with the sliding groove 511, and the cap 300 is rotated, so that the limiting rod corresponds to the limiting slot 320; finally, the movable sleeve 520 is pushed back again, so that the cap 300 is sleeved over the knob 12 to complete the assembly of the sheath adapter 20 and the knob 12, which is simple and convenient. When the handle 11 is placed on the support frame 100, and the slider portion 521 is aligned with the sliding groove 511, the movable sleeve 520 can be pushed back a small amount, so that the slider portion 521 slides into the sliding groove 511 first, and then the cap 300 is rotated so that the limiting rod corresponds to the limiting slot 320; and the movable sleeve 520 can be pushed back a small amount, it can be understood that the slider portion 521 only slides into the sliding groove 511 first, and the cap 300 maintains an appropriate distance from the knob 12, when the cap 300 is rotated, the cantilever 600 will not rotate, which can simplify the assembly process.

In a possible embodiment, the sheath adapter 20 further includes a fastener (not shown) that penetrates the fixed sleeve 510 and abuts against the movable sleeve 520, and that is threadedly connected to the fixed sleeve 510. When the assembly of the cap 300 and the knob 12 is completed, the fastener is screwed, and the movable sleeve 520 is pressed by the fastener so that the movable sleeve 520 is fixed with respect to the fixed sleeve 510, thereby preventing the cap 300 from being detached from the knob 12.

In a possible embodiment, the worm 430 may be a telescopic rod to adjust the distance of the cap 300 with respect to the telescopic rod assembly 200 to increase the adaptability of the sheath adapter 20, and the structure of the worm 430 may be the same as that of the telescopic rod assembly 200, which would not be described further herein. Further, the cantilever 600 can be configured to have the same structure as that of the telescopic sleeve assembly 500, which is not described further herein.

In the present embodiment, referring to FIGS. 1 and 4, the top of the support frame 100 is used for placing the handle 11, the bottom of the support frame 100 is provided with an input end 101 which can be connected to an output shaft 31, and the output shaft 31 can be performed transmission via the input end 101 so that the output shaft 31 drives the rotating shaft 210 to rotate. The power unit further includes an installation platform 32, and the output shaft 31 is provided on the installation platform 32. In the present embodiment, the input end 101 is provided at the bottom of the support frame 100, and when the sheath adapter 20 loaded with the surgical instrument 10 is placed on the installation platform 32, that is, when the surgical instrument 10 and the sheath adapter 20 are superposed on the installation platform 32, the docking of the input end 101 of the sheath adapter 20 and the output shaft 31 of the power unit can be achieved only by a dead load of the sheath adapter 20 and the surgical instrument 10 and the cooperation of the positioning pin 720 and the pin hole 33 at the bottom of the support frame 100, which is stable and reliable.

Specifically, the output shaft 31 of the power unit is provided with a plurality of first grooves (not shown), the input end 101 of the sheath adapter 20 is provided with a plurality of first protrusions 1011 used to be inserted into the first grooves in a one-to-one correspondence to transmit torque to facilitate the transmission connection between the sheath adapter 20 and the power unit, and the input end 101 is provided with the first protrusion 1011 to facilitate sterilization.

For example, the input end 101 may be made of magnetic material to stabilize the connection. For example, the first groove and the first protrusion 1011 are both provided in a number of two.

Figure 3:
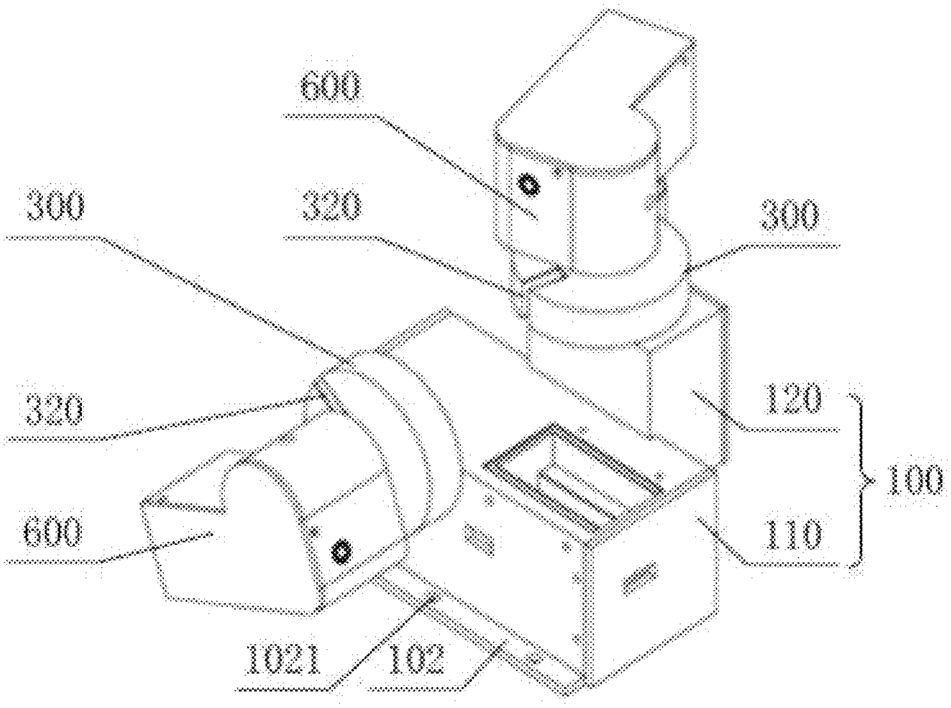
FIG. 3 is a schematic structural diagram illustrating a sheath adapter from a perspective according to the present disclosure.

In a possible embodiment, as shown in FIG. 3, the bottom of the support frame 100 extends to form a fixing portion 102 provided with at least one fixing hole 1021, and a fastening screw (not shown) passes through the fixing hole

1021 and is threadedly connected with the installation platform 32, thereby fixing the sheath adapter 20 to the installation platform 32.

In a possible embodiment, the support frame 100 is made of a magnetic material, and the support frame 100 and the installation platform 32 may be fixed through magnetic connection. In the present embodiment, it is possible to fasten without the fastening screw, making the installation operation more convenient.

In the present embodiment, and referring to FIG. 1, the sheath adapter 20 further includes a sterile barrier 700 detachably provided on the support frame 100, and the sterile barrier 700 is provided in contact with the support frame 100. In the present embodiment, the first side of the sterile barrier 700 is provided in contact with the support frame 100, and the second side of the sterile barrier 700 is provided in contact with the installation platform 32, so that the direct contact between the support frame 100 and the installation platform 32 can be effectively avoided, the contact area between the sheath adapter 20 and the power unit can be further reduced, and the probability of spread of pathogens can be reduced. In the present embodiment, the sterile barrier 700 may be a disposable accessory or may be reused after sterilization, which is not particularly limited herein.

In a possible embodiment, at least a portion of the sterile barrier 700 is configured as a magnetically attractive region that may magnetically attract the support frame 100 and the installation platform 32 to stabilize the fixation of the sheath adapter 20 with respect to the installation platform 32.

In a possible embodiment, a plurality of positioning pins 720 are provided on the sterile barrier 700, for example, two ends of the respective positioning pins 720 protrude from a first side and a second side of the sterile barrier 700 respectively, the support frame 100 and the installation platform 32 are both provided with pin holes 33 respectively corresponding to the positioning pins 720, and the positioning pins 720 are inserted into the corresponding pin holes 33, so that the sheath adapter 20 can be quickly and accurately positioned to be placed on the installation platform 32.

In a possible embodiment, the sterile barrier 700 may be replaced with a layer of sterile membrane to prevent direct contact of the support frame 100 with the installation platform 32, reducing the probability of spread of pathogens. For example, a positioning pin 720 may be provided on the installation platform 32 when a sterile membrane is provided between the support frame 100 and the installation platform 32.

In the present embodiment, continuing to refer to FIG. 1, a transmission shaft 710 is rotatably provided on the sterile barrier 700. A first end of the transmission shaft 710 is in transmission connection to an input end 101, and a second end of the transmission shaft 710 is used for transmission connection to the output shaft 31, thereby avoiding direct contact between the sheath adapter 20 and the power unit, and further reducing the probability of spread of pathogens.

Specifically, the first end of the transmission shaft 710 is provided with a plurality of second slots (not shown) respectively corresponding to the first protrusions 1011, and the second end of the transmission shaft 710 is provided with a plurality of second protrusions (not shown) respectively corresponding to the first grooves, the first protrusions 1011 are inserted into the second slots, and the second protrusions are inserted into the first grooves. For example, the transmission shaft 710 may be made of magnetic material to stabilize the connection.

Figure 2:
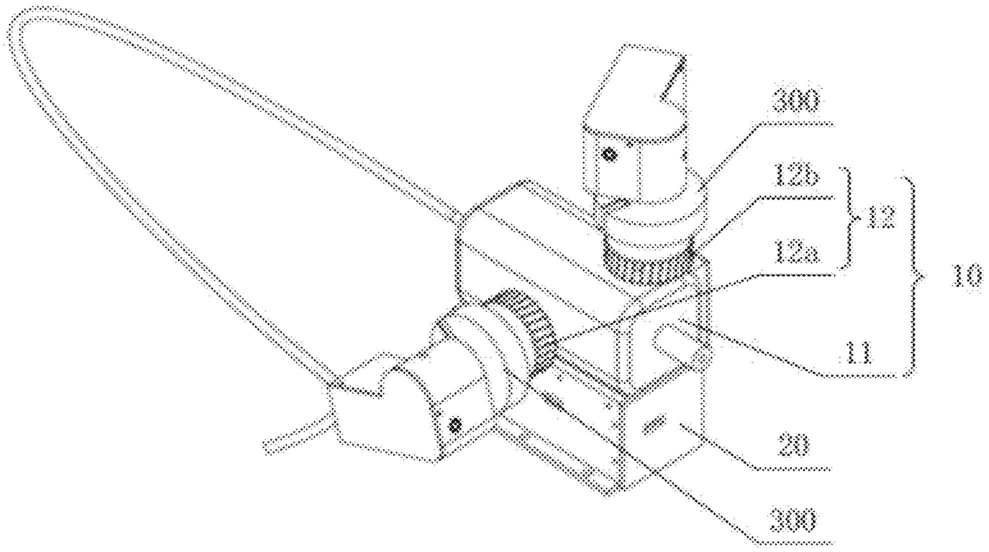
FIG. 2 is a schematic structural diagram illustrating a surgical instrument mounted to a sheath adapter according to the present disclosure.

In the present embodiment, and as shown referring to FIGS. 1 and 2, the surgical instrument 10 includes at least one knob 12. At least one transmission mechanism composed of a corresponding telescopic rod assembly 200, a cap 300, a deceleration assembly 400, a telescopic sleeve assembly 500 and a cantilever 600 is provided, and at least one transmission shaft 710 is provided on a sterile barrier 700 to improve the adaptability.

In the present embodiment, as shown referring to FIGS. 1, 2, 6 and 7, taking the surgical instrument 10 including two knobs 12 as an example, that is, the knob 12 includes a first knob 12*a* and a second knob 12*b*, the input end 101 includes a first input end 101*a* and a second output end 101*b*, the output shaft 31 includes a first output shaft 31*a* and a second output shaft 31*b*, and the transmission shaft 710 includes a first transmission shaft 710*a* and a second transmission shaft 710*b*. The first output shaft 31*a* may be in transmission connection to the first input end 101*a* through a first transmission shaft 710*a* to achieve transmission of the first knob 12*a*, and the second output shaft 31*b* may be in transmission connection to the second input end 101*b* through a second transmission shaft 710*b* to achieve transmission of the second knob 12*b*. In the present embodiment, the sheath adapter 20 is provided with two transmission mechanisms, one of which is in transmission connection to the first input end 101*a* and the other is in transmission connection to the second input end 101*b*.

Specifically, the installation platform 32 is stepped, and the installation platform 32 includes a first platform 32*a* and a second platform 32*b* provided horizontally, and a side plate 32*c* provided vertically, where the side plate 32*c* is provided between the first platform 32*a* and the second platform 32*b*, and the first output shaft 31*a* is provided on the first platform 32*a*, and the second output shaft 31*b* is provided on the second platform 32*b*. As shown in FIG. 1, the direction a is a vertical direction, the directions b and c are horizontal directions, the vertical direction is provided parallel to a plane where the direction a is located, and the horizontal direction is provided parallel to a plane where the directions b and c are located.

Further, the support frame 100 includes a first frame body 110 and a second frame body 120 provided on a first side of the first frame body 110, where the bottom of the first frame body 110 can protrude from the bottom of the second frame body 120 in a vertical direction, a first input end 101*a* is located at the bottom of the first frame body 110, and a second input end 101*b* is located at the bottom of the second frame body 120; in the present embodiment, both the first output shaft 31*a* and the second output shaft 31*b* rotate around the vertical direction; the installation platform 32 can limit the first side surface of the first frame body 110 and provide a reaction force through the side plate 32*c*, that is, the side plate 32*c* can be used to determine the relative position between the sheath adapter 20 and the power unit, and can bear the force caused by the transmission to reduce the torque received by the first input end 101*a* and the second input end 101*b*, effectively protecting the first input end 101*a*, the second input end 101*b*, the first output shaft 31*a* and the second output shaft 31*b*, and further stabilizing the fixation of the sheath adapter 20 with respect to the installation platform 32. The sterile barrier 700 is correspondingly designed in a stepped shape respect to the installation platform 32 and the support frame 100. It is obvious that, the bottom of the first frame body 110 and the bottom of the second frame body 120 may be provided in a same plane.

For example, the top of the first frame body 110 is used for placing the handle 11, the top of the second frame body 120 is provided protruding from the top of the first frame body 110 in a vertical direction, and the second frame body 120 forms a limit for the handle 11, facilitating positioning and placing the handle 11, and effectively ensuring the stability of the transmission of the surgical instrument 10 and the sheath adapter 20.

In a possible embodiment, a first knob 12*a* is provided on one side surface of the handle 11, a second knob 12*b* is provided on the top surface of the handle 11, and two transmission mechanisms are respectively provided on two opposite sides of the support frame 100 to avoid positional interference between the two transmission mechanisms. One of the two transmission mechanisms is provided on the first frame body 110, and the other is provided on the second frame body 120.

In a possible embodiment, as shown in FIG. 6, in the transmission mechanism provided on the first frame body 110, a first end of the rotating shaft 210 passes through a side of the first frame body 110 facing away from the second frame body 120 and is placed in the first frame body 110, the first end of the rotating shaft 210 can be in transmission connection to the first input end 101*a* via a transmission assembly, a second end of the rotating shaft 210 is connected to the movable shaft 220, and the cap 300 is adapted to be connected to the first knob 12*a*. The rotating shaft 210 extends in a horizontal direction, for example, in the direction c. Further, the transmission assembly includes a third bevel gear 810 and a fourth bevel gear 820, the first input end 101*a* is provided as an input shaft, the first end of the input shaft is rotatably connected to the bottom of the first frame body 110, and the first end of the input shaft is provided with a first protrusion 1011, the second end of the input shaft is provided with a third bevel gear 810, and the first end of the rotating shaft 210 is provided with a fourth bevel gear 820. The input shaft is extended in the vertical direction, and in the present embodiment, the transmission assembly is provided to guide the transmission mechanism to an appropriate position of the first frame body 110 for installation.

In a possible embodiment, as shown in FIG. 7, in the transmission mechanism provided on the second frame body 120, a first end of the rotating shaft 210 is a second output end, the first end of the rotating shaft 210 passes through the top of the second frame body 120 in a vertical direction and extends to the bottom of the second frame body 120, and the first end of the rotating shaft 210 is rotatably connected to the bottom of the second frame body 120, and the cap 300 can be placed on the top of the first frame body 110 and is adapted to be connected to the second knob 12*b*.

In the present embodiment, when the surgical instrument 10 includes more than two knobs 12, the transmission mechanism may be guided into place for installation by a gear meshing transmission assembly or other drive assembly to avoid positional interference.

For example, taking the example of the surgical instrument 10 including two knobs 12, the steps of connecting the surgical instrument 10 to the sheath adapter 20 are as follows.

First, the two movable sleeves 520 are pulled outward in a direction away from the support frame 100, and the two movable sleeves 520 are rotated so that the cantilever 600 can form clearance.

Then, the handle 11 is placed on the support frame 100, the two movable sleeves 520 are reversed, and the two caps 300 are rotated so that the limiting rods correspond to the limiting slots 320.

Finally, the two movable sleeves 520 are pushed back so that the two caps 300 are respectively sleeved over the first knob 12*a* and the second knob 12*b*, and the limiting rod and the fastener are screwed.

It should be understood that, the above-described embodiments of the present invention are merely illustrative of the present invention for purposes of clarity and are not intended to limit the embodiments of the present invention. It would be apparent to those skilled in the art that various modifications, rearrangements, and substitutions can be made without departing from the scope of the present invention. It is not necessary or possible to exhaust all the implementation methods here. It would be understood by those skilled in the art that various changes in form and details may be made therein without departing from the spirit and scope of the claims of the present invention.

What is claimed is:

1. A sheath adapter comprising:

a support frame;

a telescopic rod assembly comprising a rotating shaft and a movable shaft, the rotating shaft having a first end rotatably connected to the support frame and a second end slidably connected to a first end of the movable shaft; and a cap comprising a receiving groove, wherein the cap is connected to a second end of the movable shaft, the rotating shaft is rotatable to cause the rotation of the cap via the movable shaft, and the movable shaft is slidable in an axial direction to adjust a position of the cap with respect to the support frame.

2. The sheath adapter according to claim 1, wherein one of the rotating shaft and the movable shaft is provided with a sliding channel, and the other is slidably inserted in the sliding channel.

3. The sheath adapter according to claim 1, wherein a limiting slot is provided in a groove wall of the receiving groove.

4. The sheath adapter according to claim 1, further comprising a deceleration assembly having a first end of connected to the movable shaft and a second end of connected to the cap, wherein the rotating shaft is rotatable to cause the rotation of the cap via the movable shaft and the deceleration assembly.

5. The sheath adapter according to claim 4, further comprising:

a telescopic sleeve assembly in which the telescopic rod assembly is provided, wherein the telescopic sleeve assembly comprises a fixed sleeve fixedly connected to the support frame and a movable sleeve connected to the fixed sleeve, the movable sleeve is rotatable and slidable with respect to the fixed sleeve, and the movable sleeve is rotatably connected to the movable shaft; and a cantilever having a first end fixedly connected to the movable sleeve and a second end on which the cap is provided, wherein the deceleration assembly is provided in the cantilever.

6. The sheath adapter according to claim 5, further comprising a fastener extending through the fixed sleeve and abutting against the movable sleeve, the fastener being threadedly connected to the fixed sleeve.

7. The sheath adapter according to claim 5, wherein at least one sliding groove extending in an axial direction of the fixed sleeve is provided in the fixed sleeve, a circumferential slot communicating with the sliding groove is provided in an end of the fixed sleeve which faces the movable sleeve, a respective slider portion corresponding to each of the at least one sliding groove is provided in an end of the movable sleeve (520) which faces the fixed sleeve, and the slider portion is slidably provided in the sliding groove or the circumferential slot.

8. The sheath adapter according to claim 1, further comprising a sterile barrier detachably provided on the support frame, wherein the sterile barrier is provided in contact with the support frame.

9. The sheath adapter according to claim 8, wherein a transmission shaft is rotatably provided on the sterile barrier, a first end of the transmission shaft is detachably connected to the rotating shaft, and the transmission shaft is rotatable to cause the rotation of the rotating shaft.

10. A surgical assistance system comprising:

the sheath adapter according to claim 1; and a power unit, wherein the sheath adapter is detachably provided on the power unit, and the power unit comprises an output shaft, wherein the output shaft is rotatable to cause the rotation of the rotating shaft.

* * * * *